United States Patent [19]

Beggs et al.

[11] Patent Number: 4,479,386
[45] Date of Patent: Oct. 30, 1984

[54] INSULATION BONDING TEST SYSTEM

[75] Inventors: James M. Beggs, Washington, D.C.; Garland D. Johnston; Archie D. Coleman, both of Huntsville; Joseph N. Portwood, Decatur; Jerry M. Saunders; John W. Redmon, both of Huntsville; Allen C. Porter, Madison, all of Ala.

[73] Assignee: The United States of America as represented by the Administrator of the National Aeronautics and Space Administration, Washington, D.C.

[21] Appl. No.: 465,366

[22] Filed: Feb. 10, 1983

[51] Int. Cl.³ .................. G01M 7/00; G01N 29/04
[52] U.S. Cl. ............................. 73/582; 73/579; 73/588
[58] Field of Search ............... 73/588, 582, 602, 584, 73/586, 579

[56] References Cited

U.S. PATENT DOCUMENTS

| 3,038,329 | 6/1962 | Miller | 73/588 |
| 3,307,393 | 3/1967 | Kessler | 73/584 |
| 3,564,903 | 2/1971 | Woodmansee et al. | 73/582 |
| 4,062,229 | 12/1977 | Godfrey | 73/582 |

FOREIGN PATENT DOCUMENTS 630370 9/1978 U.S.S.R. .................. 73/584

OTHER PUBLICATIONS

"The Acoustic Impact Technique", Schroeer, *Non-Destructive Testing*, Jun. 1970, vol. 3, No. 3, pp. 194–196.

Primary Examiner—Howard A. Birmiel
Attorney, Agent, or Firm—Joseph H. Beumer; John D. Manning; Leon D. Wofford, Jr.

[57] ABSTRACT

A method and a system for testing the bonding of foam insulation (22) attached to metal. The system involves the use of an impacter (10) which has a calibrated load cell (12) mounted on a plunger (14) and a hammer head (16) mounted on the end of the plunger (14). When the impacter (10) strikes the insulation (22) at a point to be tested, the load cell (12) measures the force of the impact and the precise time interval during which the hammer head (16) is in contact with the insulation (22). This information is transmitted as an electrical signal (20) to a load cell amplifier (28) where the signal (20) is conditioned and then transmitted to a Fast Fourier Transform (FFT) analyzer (34). The FFT analyzer (34) produces energy spectral density curves (power plotted against frequency in Hertz) which are displayed on a video screen (39). An operator, by observing the frequency point at which the curve terminates, may determine the quality of the bond. Specifically, the termination frequency of the energy spectral density curve may be compared with a predetermined empirical scale to determine whether a high quality bond, good bond, or debond is present at the point of impact. For future reference and use, data from the FFT analyzer (34) are recorded on a magnetic disk (41) and/or a hard copy is produced by a printer (43).

14 Claims, 8 Drawing Figures

U.S. Patent   Oct. 30, 1984   Sheet 3 of 3   4,479,386
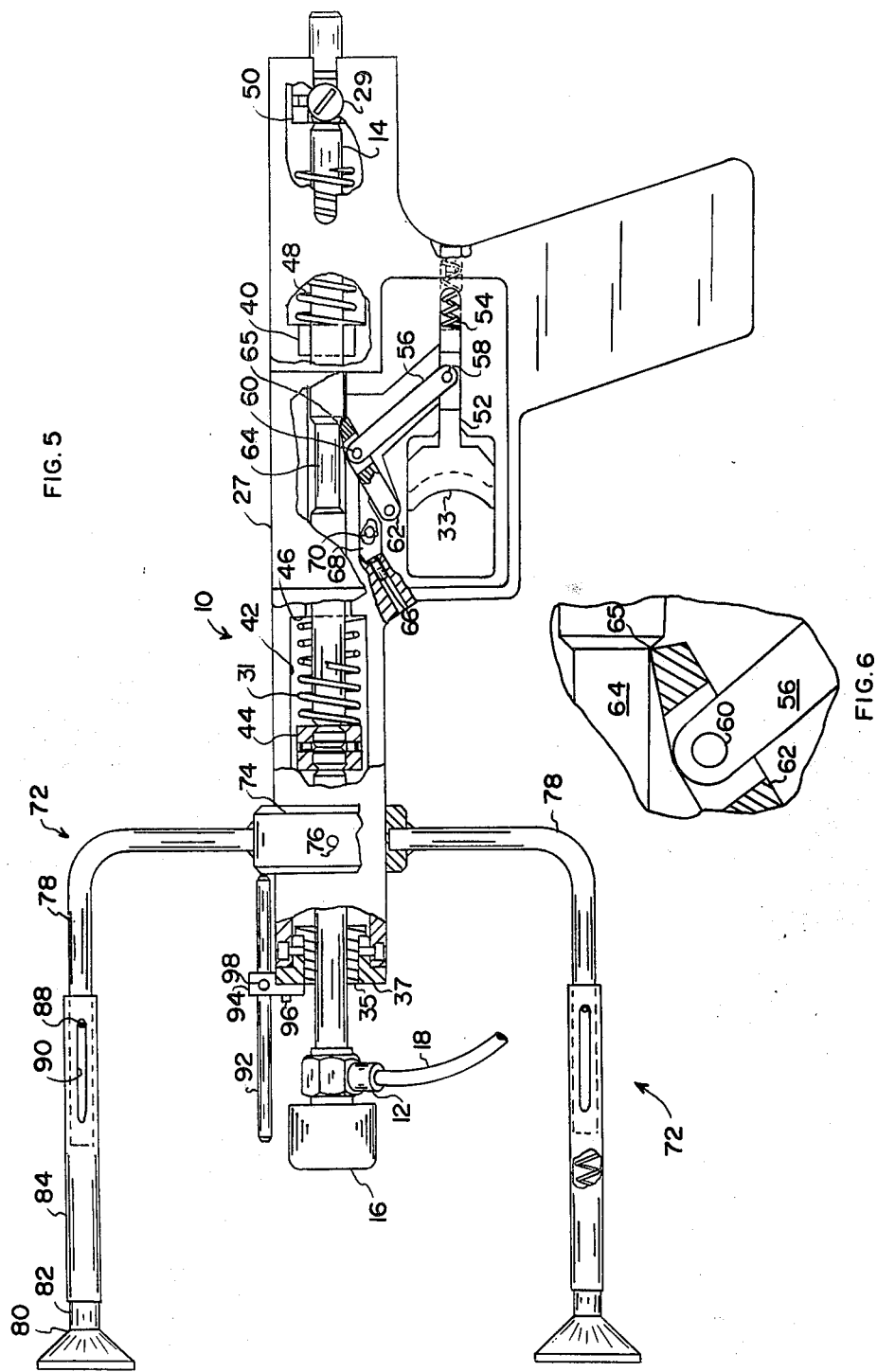

INSULATION BONDING TEST SYSTEM

ORIGIN OF THE INVENTION

The invention described herein was made in the performance of work under a NASA contract and is subject to the provisions of Section 305 of the National Aeronautics and Space Act of 1958, Pubic Law 85-568 (72 Stat. 435; 42 USC 2457).

CROSS REFERENCE TO RELATED APPLICATION

This application is related to U.S. patent application Ser. No. 460,509, filed Jan. 24, 1983, entitled "Impacting Device For Testing Insulation."

TECHNICAL FIELD

The present invention relates generally to nondestructive testing, and more particularly to a method and apparatus for testing the bonding of foam insulation attached to metal. Specifically, the invention is for testing the bonding of foam insulation sprayed on metal cryogenic fuel tanks.

BACKGROUND OF THE INVENTION

Since the advent of the space age, which began after the World War II era, the use of liquid fuel rocket engines has become commonplace. These engines use cryogenic fuels, such as liquid oxygen and liquid hydrogen. Because of the very low temperatures of these fuels in the liquid state, insulated fuel tanks were needed. The application of spray-on foam insulation has proved to be the cheapest and best way to put the required insulation on the tanks. Sometimes, however, this foam insulation does not adhere well to the metal fuel tanks. Therefore, these debonded areas must be detected and repaired so that they will not cause problems connected with the firing and use of the high altitude rockets.

At the present time, NASA has a requirement for a test system to evaluate the bonding of the insulation on the external tank for the Space Shuttle. The required testing system should: (1) be able to detect debonded areas consistent with the current quality control criteria for the external tank, (2) be non-destructive in nature, (3) include or be compatible with a method of verifying debonded areas, (4) be of a nature which could easily be used on a space vehicle, (5) have an output signal which could easily be interpreted by a technician, (6) have an output signal that could be permanently recorded, and (7) be able to test a substantial number of points in a large area in a short time.

One patent which issued to the National Aeronautics and Space Administration some years ago was U.S. Pat. No. 3,521,982 to Clotfelter et al. This device uses a variable frequency oscillator and an electro-mechanical transducer to transmit mechanical vibrations into low density insulation attached to a high density panel and receive back reflections from the low density material. The frequency of the oscillator was varied until it coincided with one of the resonant frequencies of the low density material. These resonant frequency reflections were displayed on a screen, and the amplitude of the resulting waveform provided an indication of whether the insulation was properly bonded. This system was certainly a step in the right direction, but the system did not work well enough to provide completely satisfactory operational results.

Another prior art patent is U.S. Pat. No. 3,106,838 to Crooks, which discloses a system for testing a welded joint between two pieces of metal. The Crooks device continuously impacts one of the metal pieces with an electric hammer at a frequency of two to eight times per second. A probe having an attached crystal is used to detect vibrations in the other piece of metal and change these vibrations to an electric current. This current is fed directly to an oscilloscope and displayed either as (1) a smooth and gradually decaying waveform (which indicates a good weld), or (2) a pulsating and decaying waveform (which indicates a poor weld). In the former case, the workpiece vibrates at one frequency indicating it is one piece the size of the complete welded object. In the latter case, the two pieces tend to vibrate at different frequencies, the two signals having varying phase relationships so that they will tend to interfere with each other, amplifying in some instances and dampening the vibrations in others.

U.S. Pat. No. 3,653,373 to Batterman discloses an apparatus for acoustically determining periodontal health. Batterman teaches the impacting of a tooth with an impacting device and positioning a microphone on the opposite side of the tooth in order to pick up vibrations from the tooth in the form of sound waves. Specifically, it is sound waves having the resonant frequency of the tooth which are picked up. This resonant frequency then gives an indication of whether or not the tooth is solidly rooted in its socket.

U.S. Pat. No. 3,967,498 to Pezzillo discloses a tire defect detector. The Pezzillo device has a roller with an attached handle. Inside the roller is a sound generating device comprising a hammer which hits an anvil. In operation, the Pezzillo device is placed inside a tire casing and sound is generated. The echo or return resonant signal is picked up by a microphone, and the audio signal is changed into an electrical signal. The electrical signal is compared to a predetermined scale in order to provide an indication as to whether or not the tire casing is sound.

All the inventions disclosed in the above-mentioned prior art patents have at least some utility as non-destructive test devices. However, none of the prior art patents disclose a device which could accomplish the purpose which is required of the instant invention. These prior art devices all appear to use a resonant or "signature" frequency to determine the condition of the workpiece. Conversely, as will be disclosed below, the present invention does not use a resonant frequency, but instead uses only frequency data which is sensed while the impact to the workpiece is actually taking place. Moreover, the present invention does not use a microphone to sense resonant sound waves as does Batterman and Pezzillo.

Therefore, the object of this invention is to provide a non-destructive insulation bond test system which would operate on one side of the workpiece only to locate debonded areas and also check the quality of bonds in bonded or partially bonded areas. A further object is that the part of the system which tests the workpiece be portable. A still further object is that the system provide speed and a simple decision making process.

SUMMARY OF THE INVENTION

The present invention is a method and apparatus for non-destructive testing of foam insulation attached to metal. The apparatus comprises a lightweight hammer for impacting insulation attached to metal, force measuring means mounted on the hammer for measuring the force with which the hammer strikes the insulation, means connected to the force measuring means for determining the amplitude and forced period of vibration of mechanical waves set up when the hammer strikes the insulation, and means connected to the determining means for showing a visual presentation of an energy spectral density curve for said mechanical waves. A comparison may be made between the energy spectral density curve and a predetermined empirical scale and a determination made as to whether the insulation at the point of impact is well bonded, bonded, or debonded. The method comprises the steps of: impacting insulation on metal with a calibrated impacter measuring the force of the impact and the time of the resulting force vibration, electronically generating an energy spectral density curve and visually presenting said curve on its screen, determining the frequency at which the energy spectral density curve terminates, and comparing the termination frequency of the energy spectral density curve with a predetermined empirical scale to determine whether a high quality bond, good bond, or debond is present at the point of impact.

BRIEF DESCRIPTION OF THE DRAWINGS

A presently preferred embodiment of the invention will now be described in detail in connection with the accompanying drawings, wherein:

FIG. 5 is an assembly drawing of the invention shown partially in section and with the housing partially cut away in order to show the parts.

FIG. 6 is an enlarged cut-away view showing how the sear holds the plunger in its cocked position.

DETAILED DESCRIPTION OF THE INVENTION

Figure 1:
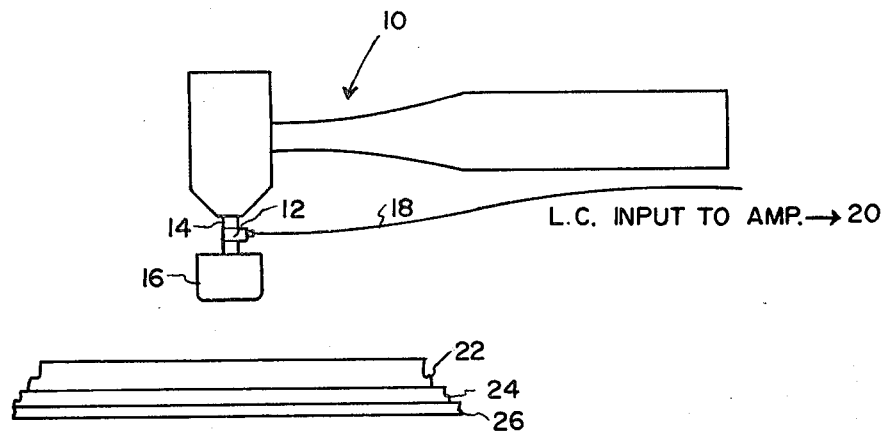
FIG. 1 is a schematic diagram of part of the invention in position to impact insulation in order to obtain basic data.

FIG. 1 is a schematic diagram of part of a preferred embodiment of the present invention. The basic equipment used in the prototype system to obtain the data needed to evaluate the bond between insulation and a metal cryogenic fuel tank is shown. The system involves the use of an impacter or lightweight hammer, shown generally at 10, which has a calibrated load cell 12 mounted on a moving rod or plunger 14. The load cell used in the prototype device is PCB Model 208A03, which is commercially available from Piezotronics, Inc. The power supply for the load cell is PCB Model 480D06. An impact hammer head 16 is mounted at the end of plunger 14. Cable 18 carries force measurement data 20 from load cell 12 to other elements of the system for processing and use in evaluating the quality of bonding of the insulation as will be described hereinbelow.

As can be seen in FIG. 1, lightweight hammer 10 is poised, ready to impact a layer of spray-on foam insulation 22. Insulation 22 is attached to a layer of an ablating material 24, which in turn is attached to a metal substrate 26. This metal substrate, in this instance, is the wall of an aluminum alloy fuel tank (the external tank of the Space Shuttle). The ablating material is applied under the foam to the front and back ends of the external tank and to other areas where aerodynamic heating is most severe during flight. The ablating material is designed to prevent heat transfer to the cryogenic fuel in the tanks.

Figure 2:
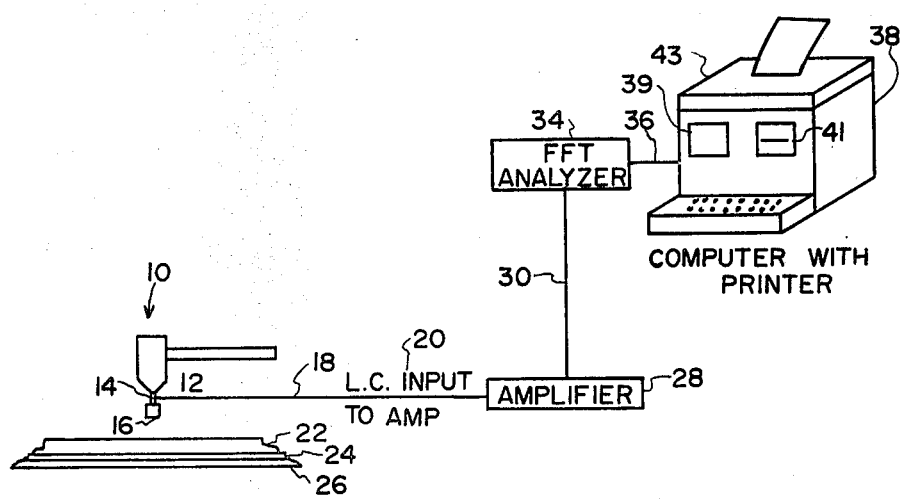
FIG. 2 is a schematic diagram of the invention.

Looking now at FIG. 2, there is shown a block diagram of the bond test system. In addition to the parts of the system already discussed for FIG. 1, it will be noted that cable 18 carries force measurement data 20 to a load cell amplifier 28. Amplifier 28 conditions data 20 and changes it to a voltage signal which is compatible with analyzer 34. The output 30 of load cell amplifier 28 is fed to a Fast Fourier Transform (FFT) analyzer 34. FFT analyzer 34 is connected by a cable 36 to a desktop computer 38 which has a video display 39 and mass storage compartment 41. FFT analyzer 34 is a commercially available Hewlett-Packard structural dynamics analyzer, Model HP5423A, connected to a Hewlett-Packard Model HP9826 desktop computer 38. A Hewlett-Packard Model HP2673A printer 43 is connected to computer 38. As indicated above, one of the basic concepts of this invention involves the use of an impacting device 10 to apply a very low force impact to the insulation. Load cell 12 measures the force and duration of the impact and transmits data 20 to remote equipment where it may be read out as a single pulse. The period of time during which the impact is being applied to the insulation is called the forced vibration period. For the type of sprayed-on foam insulation presently being used on the external tank of the Space Shuttle, this period is in the range of 5 to 12 milliseconds in duration and averages about 8 milliseconds. It should be noted that this forced vibration period will vary with different insulation materials, thickness of the insulation, different bonding materials, and so forth. Load cell 12 senses only during this forced vibration period so that, after the force is removed, there is no further signal on the load cell. The signal generated by load cell 12 is a direct and instantaneous measure of the local stiffness of insulating material 22 at the point of impact. If insulation 22 is well bonded to the metal substrate, the stiffness or impedance will be much higher, causing a shorter duration pulse. The energy spectral density curve (or power spectrum curve) of the pulse obtained from a bonded point will display frequencies of 440 Hertz and above. The energy spectral density curve of the pulse obtained from a very well bonded point will display frequencies of 520 Hertz and above. The energy spectral density curve of the pulse obtained from a debonded point will show only frequencies below 360 Hertz because the insulation alone (not bonded) does not have the stiffness to support energy at the high frequencies. This will be explained in more detail with regard to FIGS. 3 and 4 below.

Figure 3:
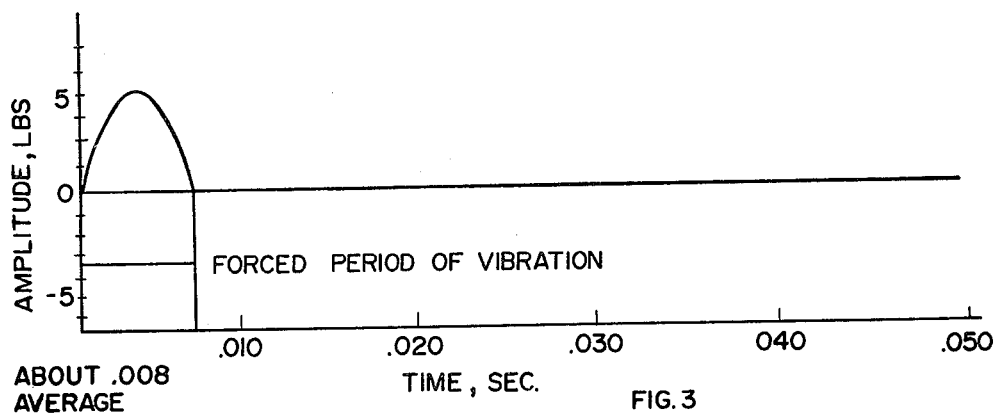
FIG. 3 is a graph showing a time history of load cell measurement.

FIG. 3 shows a typical time history of the forced period of vibration as it is fed to the on-line Fast Fourier Transform (FFT) analyzer 34. Fast Fourier Transform analyzer 34 takes this time history and rapidly converts it to its respective amplitude versus frequency curve in order to enable the operator to make the final decision as to the condition of the bonding. This frequency conversion made by the Fast Fourier Transform analyzer takes less than one second.

Figure 4A:
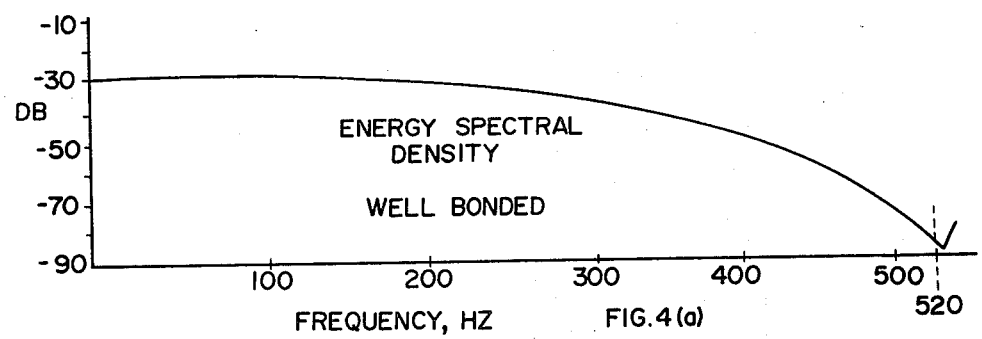
FIG. 4a is a graph showing the energy spectral density curve of well bonded insulation.
Figure 4B:
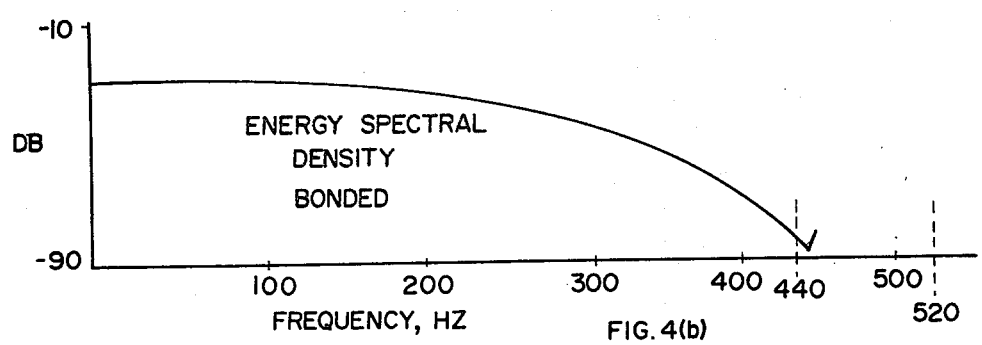
FIG. 4b is a graph showing the energy spectral density curve of bonded insulation.
Figure 4C:
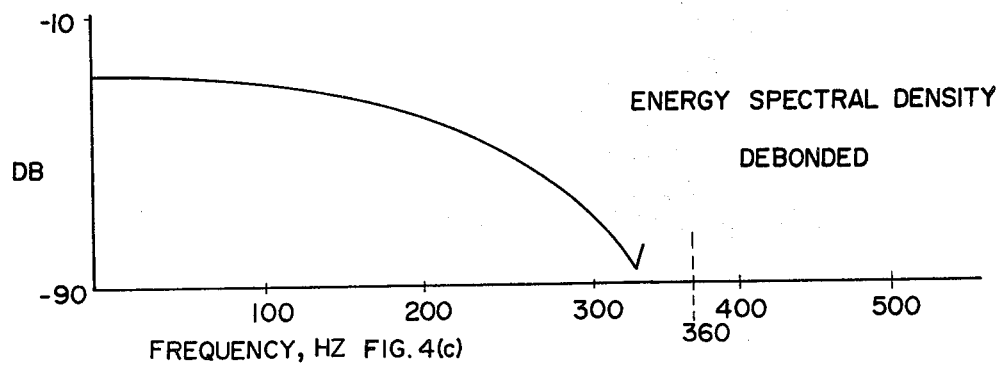
FIG. 4c is a graph showing the energy spectral density curve of debonded insulation.

FIGS. 4a, 4b, and 4c show typical cases of energy spectral density curves for areas which are well bonded, bonded, and debonded, respectively. These curves produced by the FFT analyzer are arranged to plot a unit of power (pounds-seconds/Hertz or db) against frequency in Hertz. When the frequency conversion is made by the FFT analyzer, the operator need only observe one feature of the curve to determine the quality of the bond. First, he observes the point at which the curve terminates. As may be seen in Fig. 4a, if it is above 520 Hertz for thick insulation, this is an indication of excellent bonding. If the curve terminates in the range from 440 Hertz to 520 Hertz, this is an indication of good bonding, as shown in FIG. 4b. Conversely, when the energy spectral density curve terminates below 360 Hertz, it is an indication that a debond exists, as shown in FIG. 4c.

FIG. 5 shows an assembly drawing of the preferred embodiment of impacter 10, with part of the device in section, and with part of case 27 cut away in order to show the arrangement of the parts. Case 27 is designed to be approximately the same size and shape as the U.S. Army .45-caliber automatic pistol. Plunger 14 is a one-piece, long metal rod which extends completely through the upper part of case 27 and protrudes from both the front and back ends of case 27. Plunger 14 may be cocked by grasping the two guides 29 located at the rear end of plunger 14 and pulling plunger 14 to the rear, thus compressing the front or driving spring 31. When plunger 14 is released by trigger 33, driving spring 31 drives the plunger forward so that it may perform its impacting function.

Plunger 14 is supported in case 27 by a forward bushing 35 mounted in end fitting 37 and by rear bushing 40 located directly above the handle. Load cell 12 is attached to the front end of plunger 14. Hammer head 16 is in turn attached to the front end of load cell 12. Hammer head 16, which preferably is made of an epoxy fiberglass, may be formed with a flat front impacting surface, as shown in FIG. 5. Preferably, however, the front impacting surface of hammer head 16 is slightly rounded so that the lightweight hammer will deliver uniform impacting blows even if the impacter is canted at a slight angle to the workpiece.

The front or driving spring 31 is located in a circular driving spring recess 42 located in the rear end of the barrel area of impacter 10. Driving spring 31 is retained under compression by front spring stop 44 and by the rear surface 46 of the barrel area. Front spring 31 may be provided in several wire diameters, giving several different spring rates, as desired.

Rear spring 48 surrounds plunger 14 in the upper rear section of case 27. Rear spring 48 provides a cushioning effect when front spring 31 drives the plunger forward. As plunger 14 travels forward under the driving force of front spring 31, rear spring 48 is compressed, thereby slowing the plunger down immediately after hammer head 16 impacts the workpiece. This prevents hammer head 16 from bouncing or impacting insulation 22 more than once. Spring 48 is retained between rear bushing 40, which also acts as a forward stop for spring 48 and by stop 50, which is attached to the rear end of plunger 14. As plunger 14 goes forward, stop 50 contacts spring 48 and compresses it, thus providing the aforementioned cushioning effect.

Impacter 10 has a precisely adjustable trigger mechanism. When trigger 33 is pulled to the rear, trigger projection 52 contacts trigger spring 54 and compresses it. At the same time, trigger projection 52 takes the lower end of trigger link 56 to the rear with it. Trigger link 56 is pivotally connected by upper trigger link pin 60 to sear 62. A pull on trigger link 56 exerts a downward pull on sear 62 and causes the tip of sear 62 to come out of machined notch 65 at the rear end of machined step 64 in plunger 14.

The trigger mechanism has a very precise adjustment. When set screw 66 is turned inward, the forward end of sear adjuster 68 is caused to move upward, and sear adjuster 68 rotates about pin 70. This causes the rear end of sear adjuster 68 to push downward on sear 62, thus adjusting the precise point where the tip of sear 62 contacts the rear end of machined step 64 in plunger 14. Preferably, the tip of sear 62 will be seated in notch 65. This provides a very precise adjustment on both trigger pull and operation of the trigger mechanism.

To provide stability to impacter 10 during the time when the device is impacting the insulation, location guide assembly 72 is attached to the front end of the barrel area. Sleeve 74 fits over the outside of the barrel and is fastened to the barrel by two set screws 76. Extending straight out from circular sleeve 74 are two location guide rods 78. These location guide rods 78 extend out from circular sleeve 74 about three to four inches on the prototype device and are then bent forward at a 90° angle. Bumper 80 is attached to bumper rod 82, which is slidably attached to each of the two location guide rods 78. Guide rod sleeve 84 holds each of the two bumper rods 82 on its respective guide rod 78. Each guide rod sleeve 84 is attached to its respective guide rod 78 by a pin 88 attached to guide rod 78. Each pin 88 rides on a slot 90 in each guide rod sleeve 84. When impacter 10 is pushed against the workpiece, bumpers 80 contact the workpiece first and cause bumper rods 82 to compress guide rod springs 86. As will be apparent from the above discussion of the design of the location guide assembly, sleeve 74 may be oriented so that location guide rods 78 are either at the sides of the barrel area or above and below it, whichever may be desired by the operator.

An additional gauge on impacter 10 is provided by gauge rod 92 which is mounted at the end of the barrel area. Rod 92 is attached to end fitting 38 by bracket 94 and studs 96. Rod 92 may be slid forward and backward by adjusting set screw 98. This provides a way for the operator to see and have a "feel" for the distance to hold impacter 10 from the insulation, as may be desired by the operator or required by the type of insulation being tested.

FIG. 6 is an enlarged cut-away view of the relationship between sear 62 and plunger 14 and shows how the sear holds the plunger in its cocked position.

Going now to the operation of the preferred embodiment of the system as shown in FIG. 2, impact hammer 10 is released from its cocked position by pulling trigger 34 so that hammer head 16 impacts sprayed-on foam insulation 22. For the duration of the time hammer head 16 is in contact with insulation 22 (forced period of vibration), load cell 12 senses data 20 and transmits it to amplifier 28. To avoid any possible loss of the data signal, the FFT analyzer is set up in a pre-trigger mode. A conditioned signal is then transmitted on to FFT analyzer 34, which is connected to a desktop computer 38 with video display on screen 39. The frequency at which the energy spectral density curve terminates is compared with an empirical scale to enable the operator to make a determination of whether the point of impact is well bonded, bonded, or debonded. Data from FFT analyzer 34 may also be recorded in permanent form on a disk. Optionally, this data may also be dumped to printer 43 to produce a hard copy.

In practice, the system is used to test a large number of points in succession, using a matrix and following a set procedure. Impact points in the matrix are tested in a particular pre-arranged order and following a particular pattern. Computer 38 keeps a record of the test results for each impact point on the insulation according to its coordinates in the matrix. When the testing is complete, computer 38 can map the tested area and indicate bonded and debonded areas.

The present invention has been specifically described for purposes of illustration as being used in testing portions of the exterior walls of the external tank of the Space Shuttle, consisting of curved metal plates having a foam composite sprayed on them. However, it is obvious that the invention also finds utility in the testing of panels composed of a wide variety of other kinds of materials.

The nature and scope of the present invention having been indicated and the preferred embodiment of the invention having been specifically described, what is claimed is:

1. A system for testing the bonding of insulation attached to metal comprising:
    a hammer for impacting insulation attached to metal, said hammer comprising means for measuring the force with which said hammer strikes said insulation and the time duration of the impact and generating an electrical signal representing said force and said time duration;
    conditioning means for transforming said electrical signal by amplifying the voltage, said conditioning means having a high input impedance and a low output impedance; and
    means connected to said conditioning means for using said conditioned signal for determining spectral data representing the amplitude and forced period of vibration of mechanical waves set up when said hammer strikes said insulation and transforming said data into data representing an energy spectral density curve for said mechanical waves, said determining means comprising means for showing a visual presentation of an energy spectral density curve;
    whereby, a comparison may be made between said energy spectral density durve and a predetermined empirical scale and a determination made as to whether: insulation at the point of impact is well bonded, bonded, or debonded.

2. The system of claim 1 wherein said hammer comprises a spring-loaded plunger.

3. The system of claim 2 wherein said measuring means comprises a load cell mounted on said plunger.

4. The system of claim 1 wherein said conditioning means comprises a load cell amplifier.

5. The system of claim 4 wherein said determining means is a Fast Fourier Transform analyzer.

6. The system of claim 5 comprising recording means for recording data from said conditioning means.

7. The system of claim 6 wherein said hammer comprises a spring-loaded plunger.

8. The system of claim 7 wherein said hammer comprises a load cell mounted on said plunger.

9. The system of claim 8 wherein said recording means comprises a magnetic disk for recording data from said determining means.

10. The system of claim 8 wherein said recording means comprises a printer for recording data from said determining means.

11. A method for testing the bonding of insulation attached to metal comprising the steps of:
    imparting insulation attached to metal with a calibrated impacter measuring the force of the impact and the time duration of the resulting force vibration;
    generating an electrical signal which is representative of said force and said time duration;
    electronically transforming said electrical signal into an energy spectral density curve and visually presenting said curve on a screen;
    determining the frequency at which said energy spectral density curve terminates; and
    comparing the termination frequency of said energy spectral density curve with a predetermined empirical scale to determine whether a high quality bond, bond, or debond is present at the point of impact.

12. The method of claim 11 comprisisng conditioning said electrical signal before electronically transforming said electrical signal to said energy spectral density curve.

13. The method of claim 12 comprising electromagnetically recording the data from said energy spectral density curve in order to preserve it.

14. The method of claim 12 including using a printer for recording the data from said energy spectral density curve in order to preserve it.

* * * * *